United States Patent
Kølle

(10) Patent No.: US 10,751,276 B2
(45) Date of Patent: Aug. 25, 2020

(54) LIPOFILLING WITH EX-VIVO EXPANDED ADIPOSE TISSUE-DERIVED STEM CELLS FOR COSMETIC BREAST FILLING OR FOR FACIAL FILLING AND/OR REJUVENATION

(71) Applicant: Stemform ApS, Charlottenlund (DK)

(72) Inventor: Stig-Frederik Trojahn Kølle, Charlottenlund (DK)

(73) Assignee: STEMFORM APS, Charlottenlund (DK)

( * ) Notice: Subject to any disclaimer, the term of this patent is extended or adjusted under 35 U.S.C. 154(b) by 0 days.

(21) Appl. No.: 14/899,351

(22) PCT Filed: Jun. 26, 2014

(86) PCT No.: PCT/EP2014/063581
§ 371 (c)(1),
(2) Date: Dec. 17, 2015

(87) PCT Pub. No.: WO2014/207135
PCT Pub. Date: Dec. 31, 2014

(65) Prior Publication Data
US 2016/0113863 A1    Apr. 28, 2016

Related U.S. Application Data

(60) Provisional application No. 61/839,578, filed on Jun. 26, 2013.

(51) Int. Cl.
| A61K 8/98  | (2006.01) |
| A61L 27/38 | (2006.01) |
| A61L 27/36 | (2006.01) |
| A61Q 19/00 | (2006.01) |

(52) U.S. Cl.
CPC .......... *A61K 8/981* (2013.01); *A61L 27/3604* (2013.01); *A61L 27/3804* (2013.01); *A61Q 19/00* (2013.01); *A61K 2800/91* (2013.01); *A61L 2400/06* (2013.01); *A61L 2430/04* (2013.01); *A61L 2430/34* (2013.01)

(58) Field of Classification Search
None
See application file for complete search history.

(56) References Cited

U.S. PATENT DOCUMENTS

2005/0025755 A1* 2/2005 Hedrick ............ A61L 27/3604
                                                       424/93.21
2010/0279405 A1  11/2010 Peterson et al.

FOREIGN PATENT DOCUMENTS

DE    10 2011 121    4/2013

OTHER PUBLICATIONS

Ko et al., International Journal of Medical Sciences, 2011; 8(3):231-238.*
Pu et al., Asthetic Surgery Journal, 2006, vol. 26, No. 6, pp. 653-661.*
Written Opinion and International Search Report dated Oct. 30, 2014 in International Application No. PCT/EP2014/063581.
Database WPI, Week 201212, Thomson Scientific, London, GB; AN 2012-A53349, XP002731438 & CN 102 284 084 A (Wang Y) Dec. 21, 2011 (Dec. 21, 2011) abstract.
Sterodimas, et al, "Cell-Assisted Lipotransfer", pp. 78-81, Jan. 1, 2010, vol. 30, No. 1, Aesthetic Surgery Journal, Mosby-Year Book, St. Louis, MO, US, XP009148139.
Leuchter, et al., "Treatment of velopharyngeal insufficiency by autologous fat injection", 2010, pp. 977-983, vol. 267, Eur Arch Otorhinolaryngol.
Coleman, et al., "Structural Fat Grafting: More Than a Permanent Filler", Sep. 1 Supplement, 2006, pp. 108S-120S, vol. 118, No. 3S, Plastic and Reconstructive Surgery.
Lu, et al., "Improvement of the Survival of Human Autologous Fat Transplantation by Using VEGF-Transfected Adipose-Derived Stem Cells", Nov. 2009, pp. 1437-1446, vol. 124, No. 5, Plastic and Reconstructive Surgery.
Kolle, et al., "Enrichment of autologous fat grafts with ex-vivo expanded adipose tissue-derived stem cells for graft survival: a randomized placebo-controlled trial", Sep. 28, 2013, pp. 1113-1120, vol. 382, The Lancet.
Schallmoser, et al., "Human platelet lysate can replace fetal bovine serum for clinical-scale expansion of functional mesenchyman stromal cells" Aug. 2007, pp. 1436-1446, vol. 47, Transfusion.
Yoshimura, et al, "Cell-Assisted Lipotransfer for Cosmetic Breast Augmentation: Supportive Use of Adipose-Derived Stem/Stromal Cells", 2008, pp. 48-55, vol. 32, Aesth Plast Surg.
Matsumoto, et al., "Cell-Assisted Lipotransfer: Supportive Use of Human Adipose-Derived Cells for Soft Tissue Augmentation with Lipoinjection", 2006, pp. 3375-3382, vol. 12, No. 12, Tissue Engineering.
Rasmussen, et al., "Prolonged hypoxic culture and trypsinization increase the pro-angiogenic potential of human adipose tissue-derived stem cells", 2011, pp. 318-328, vol. 13, Cytotherapy.
Thangarajah, et al., "IFATS Collection: Adipose Stromal Cells Adopt a Proangiogenic Phenotype Under the Influence of Hypoxia", 2009, pp. 266-274, vol. 27, Stem Cells.
Rehman, et al., "Secretion of Angiogenic and Antiapoptotic Factors by Human Adipose Stromal Cells", 2004, pp. 1292-1298, Circulation.
Peltoniemi, et al., "Stem cell enrichment does not warrant a higher graft survival in lipofilling of the breast: A prospective comparative study", 2013, pp. 1494-1503, vol. 66, Journal of Plastic, Reconstructive & Aesthetic Surgery.

(Continued)

Primary Examiner — Scott Long
Assistant Examiner — E. Yvonne Pyla
(74) Attorney, Agent, or Firm — Foley & Lardner LLP

(57) ABSTRACT

The present invention relates to a composition comprising ex-vivo expanded adipose tissue derived stem cell (ASC) or ex-vivo expanded adipose tissue-derived stem cells (ASC) mixed with harvested fat tissue at a ratio of $5.0 \times 10^4$-$2.0 \times 10^8$ ASCs/mL fat; for example $1.0 \times 10^5$-$2.0 \times 10^7$ and the use of ex-vivo expanded adipose tissue-derived stem cells or ex-vivo expanded adipose tissue-derived stem cell enriched fat grafts as an agent for cosmetic breast filling/augmentation or for facial filling/reju-venation.

7 Claims, 14 Drawing Sheets

(56) References Cited

OTHER PUBLICATIONS

Figure 1:
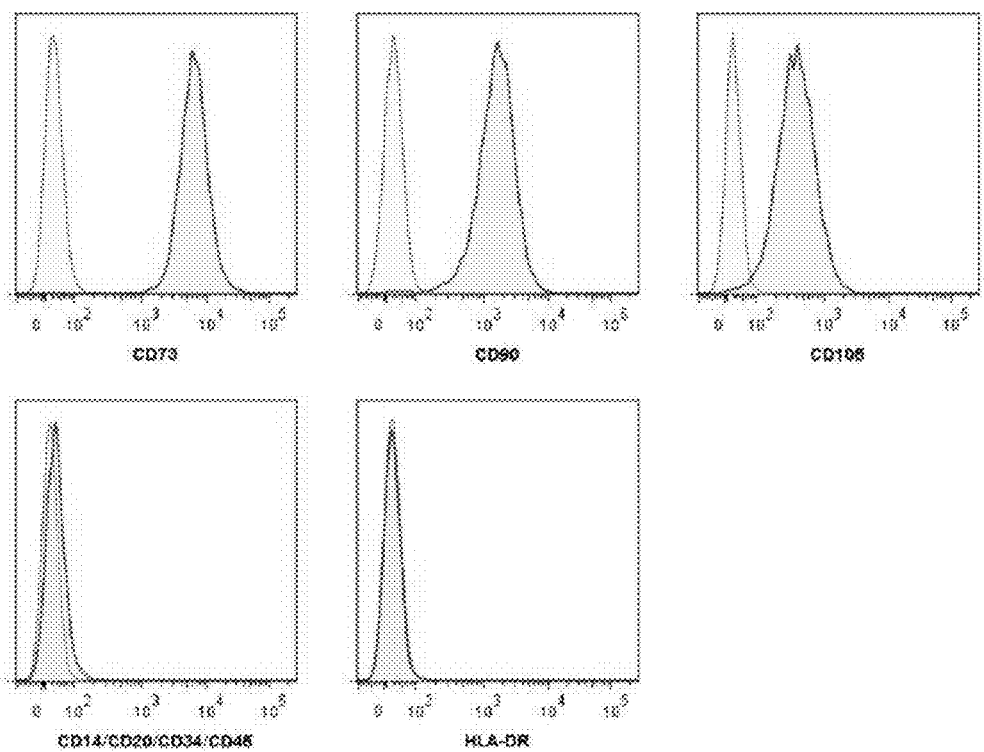
Figures 2A, 2B, 2C, 2D, 2E, 2F:
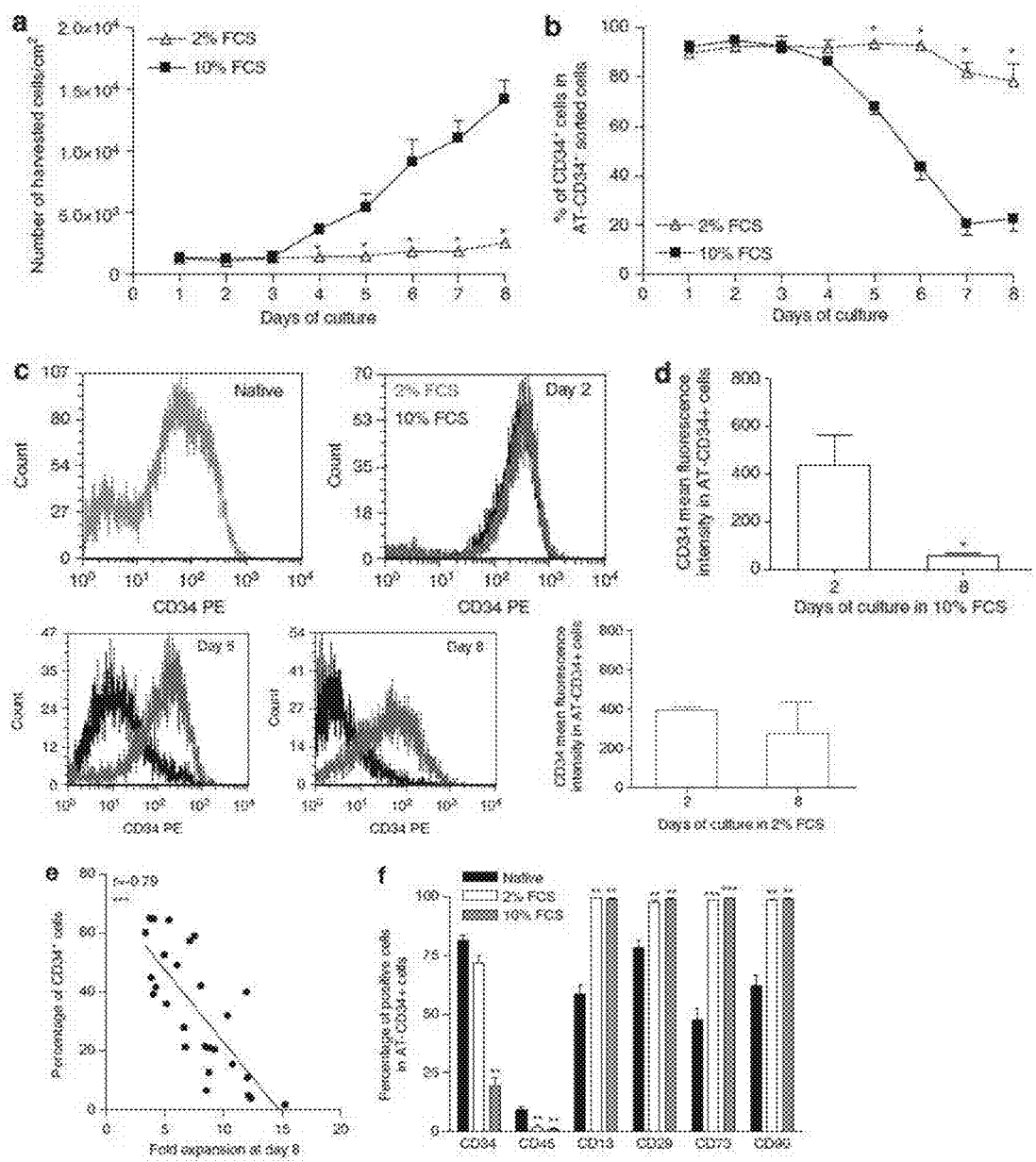
Figures 3A, 3B, 3C, 3D:
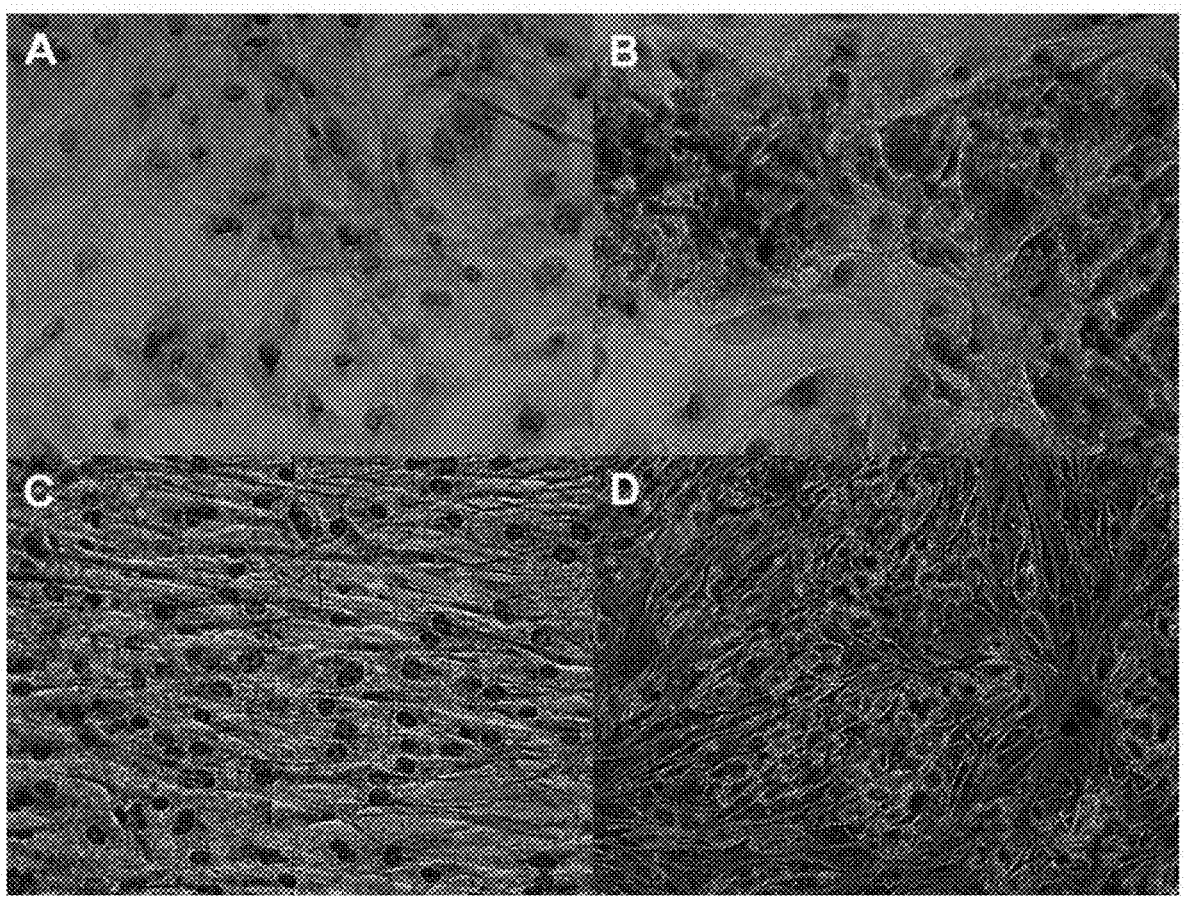
Figure 3E:
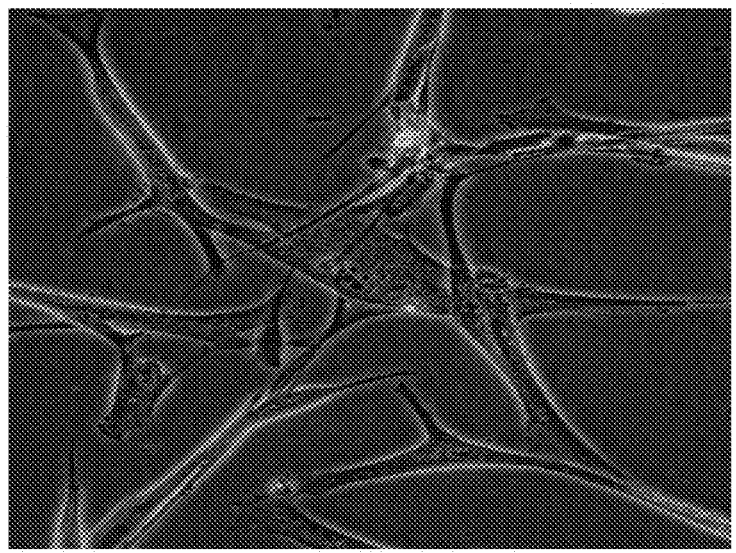
Figure 4:
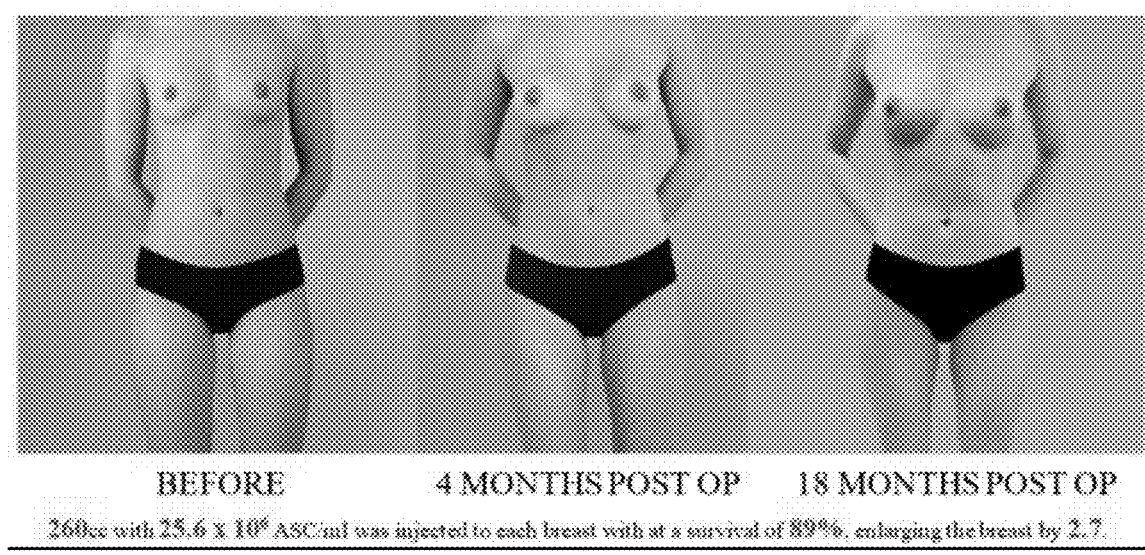
Figure 5:
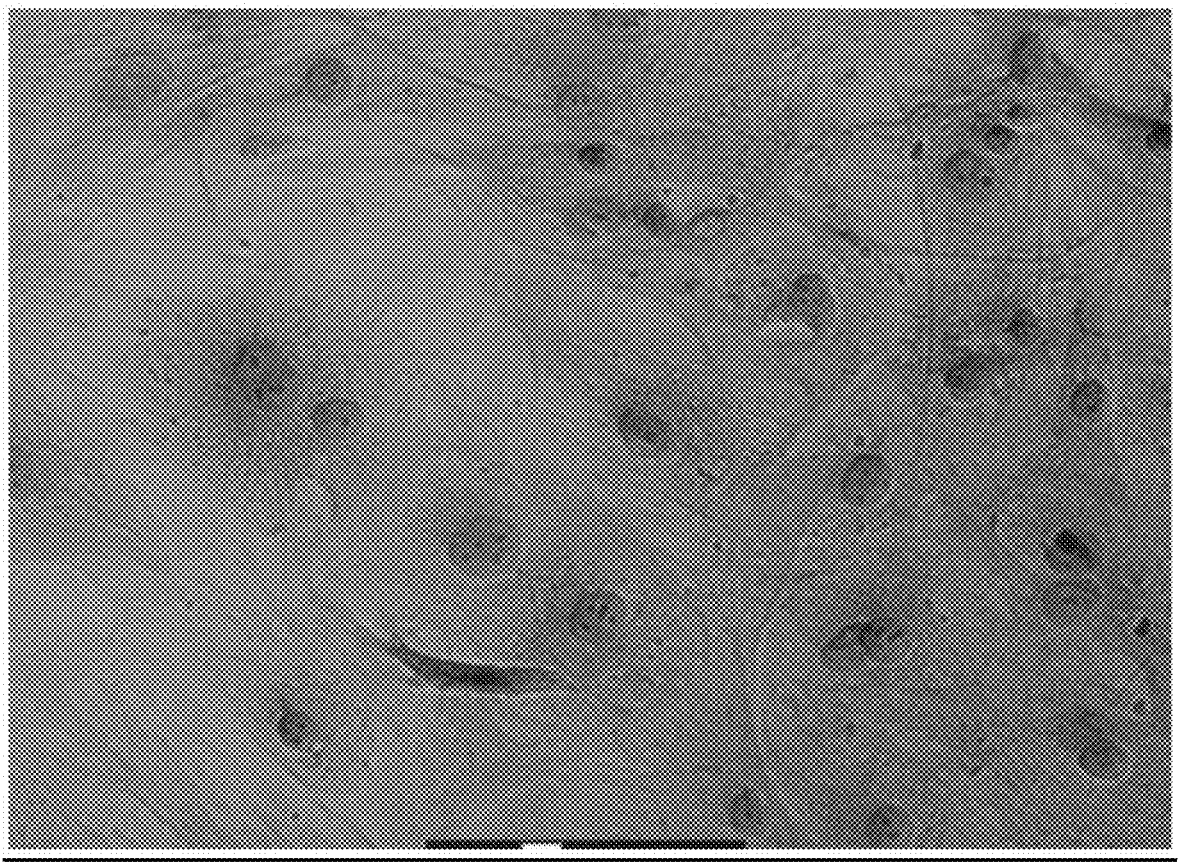
Figure 6:
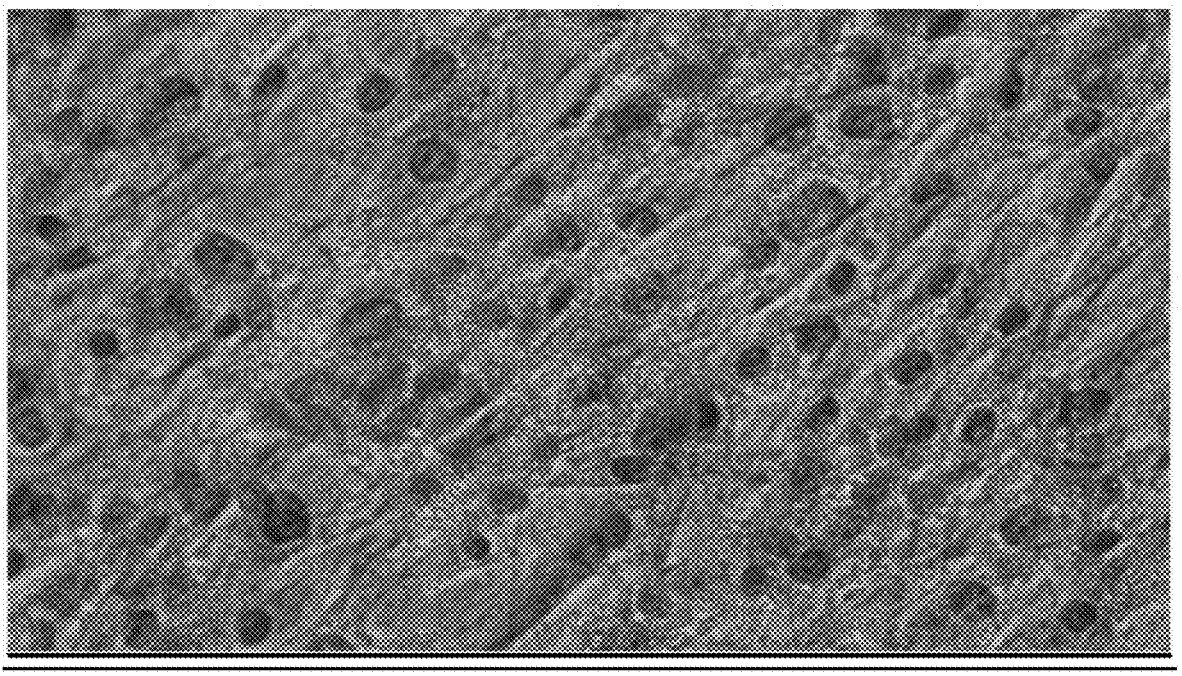
Figure 7:
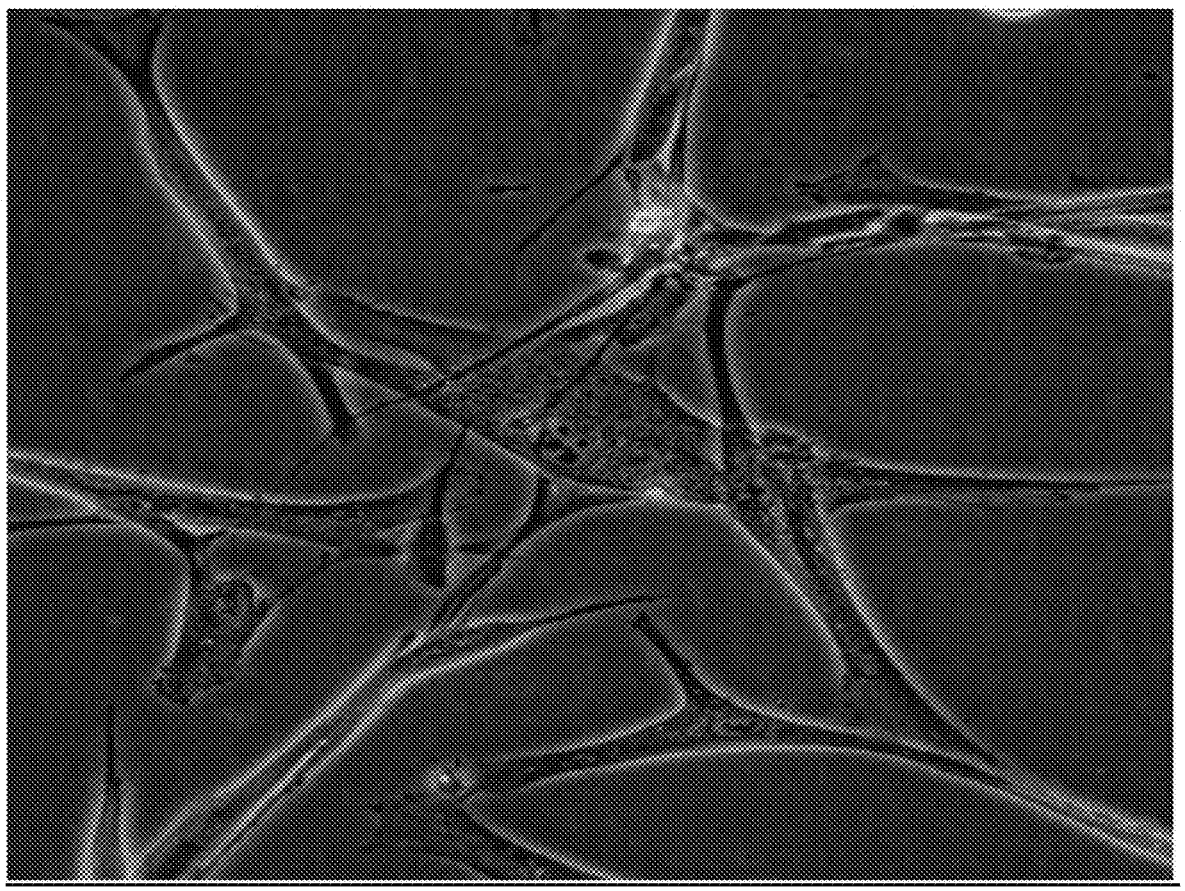
Figure 8:
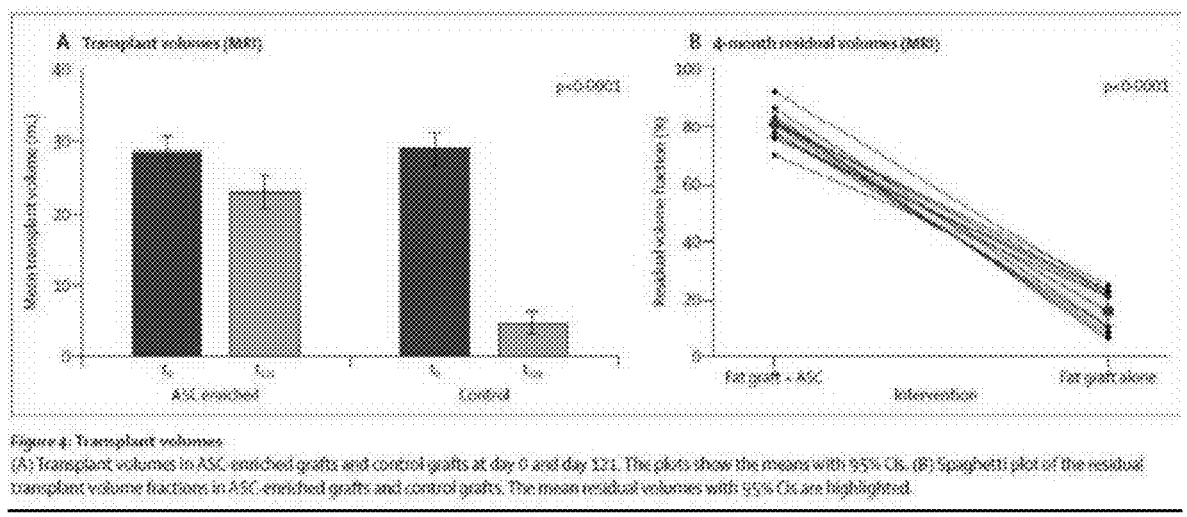
Figure 9:
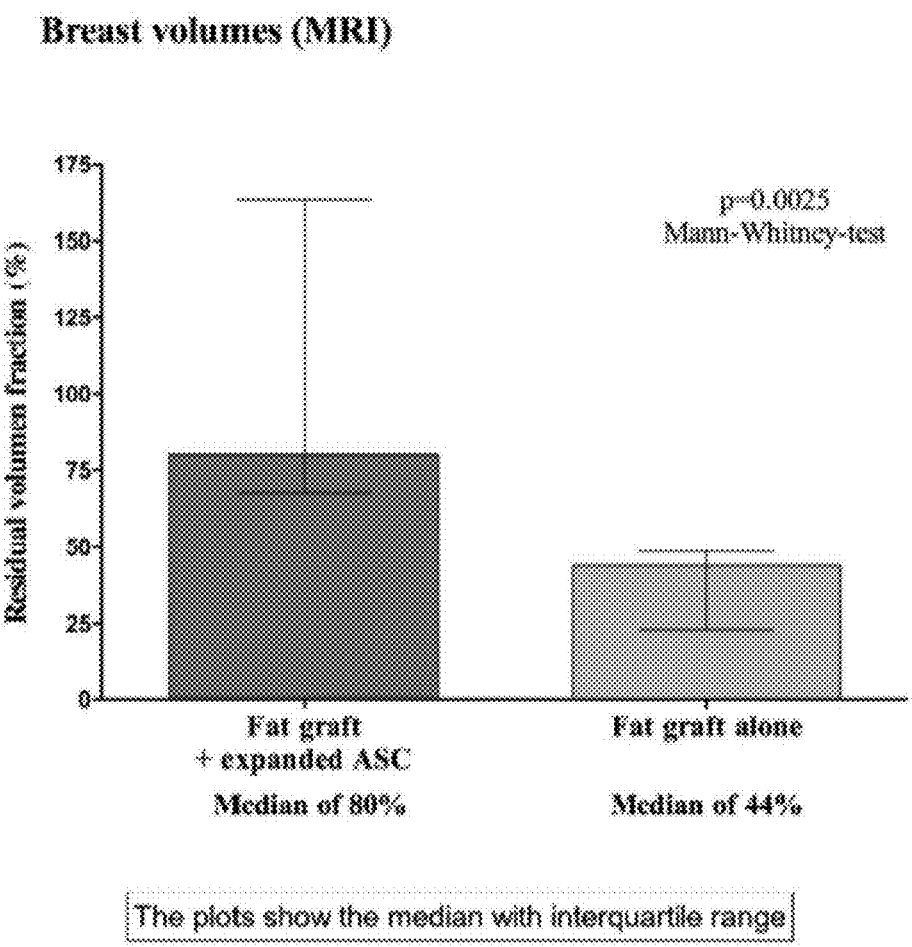
Figure 10:
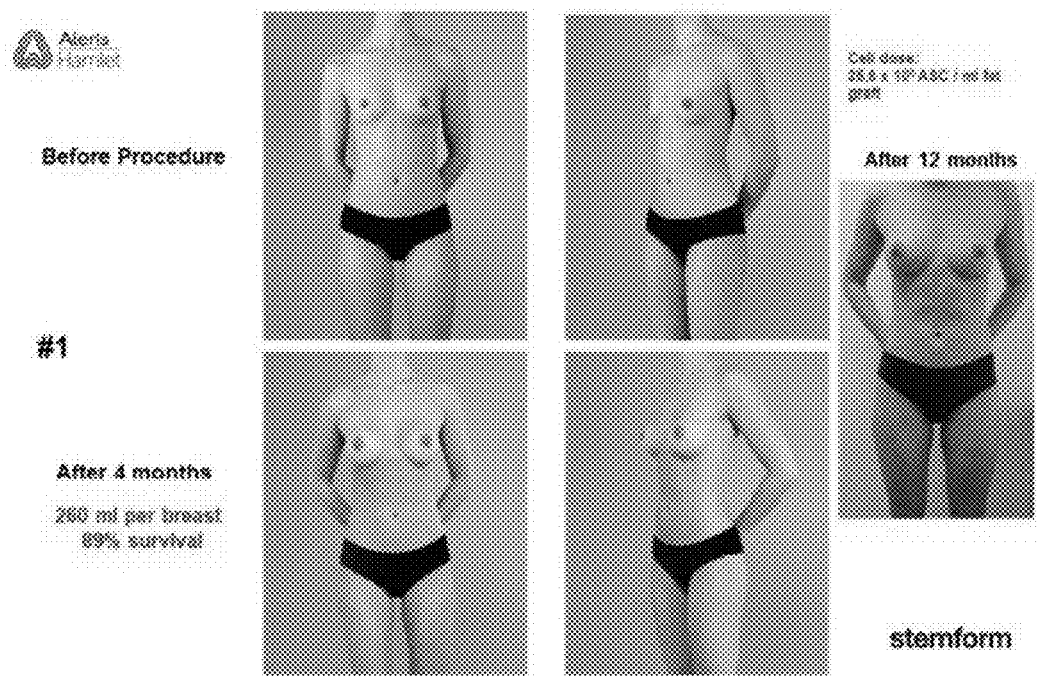
Figure 11:
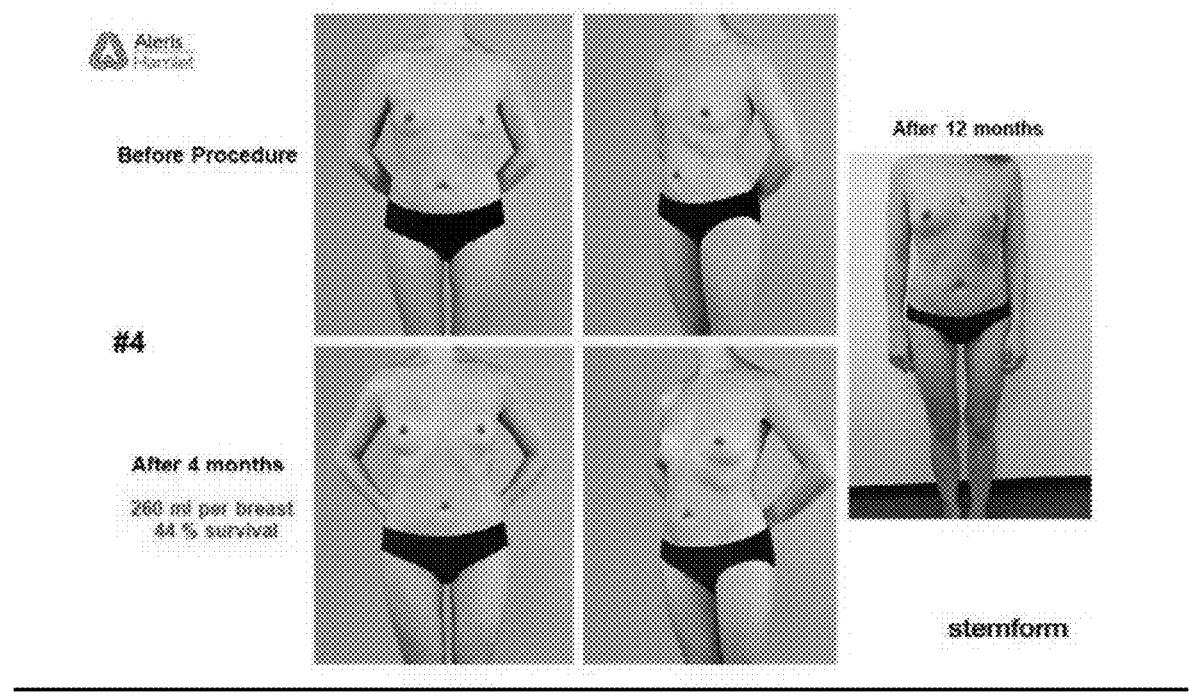
Figure 12:
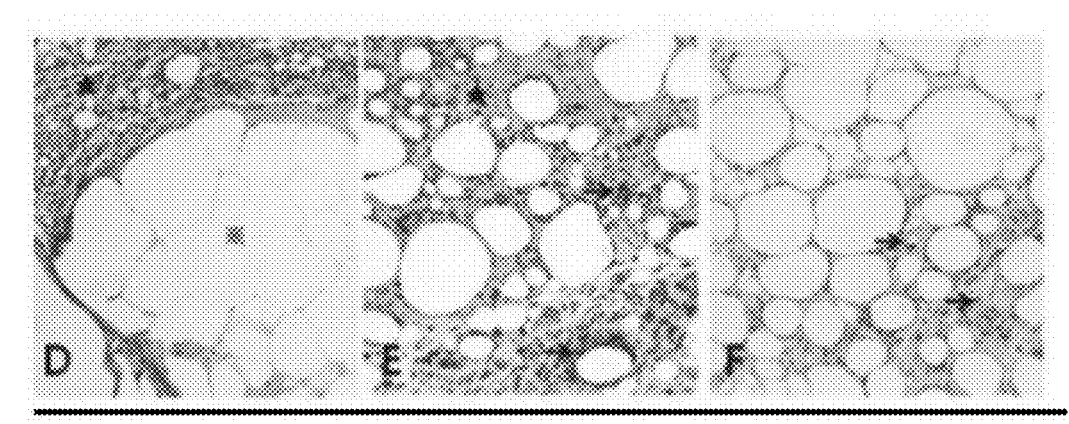
Figure 13:
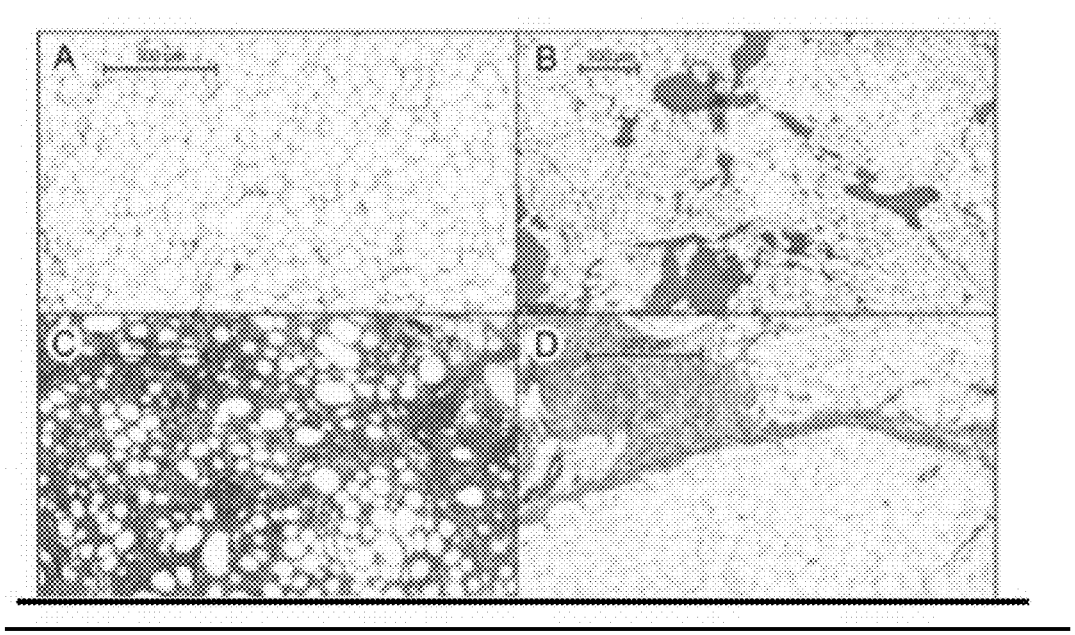
Figure 14:
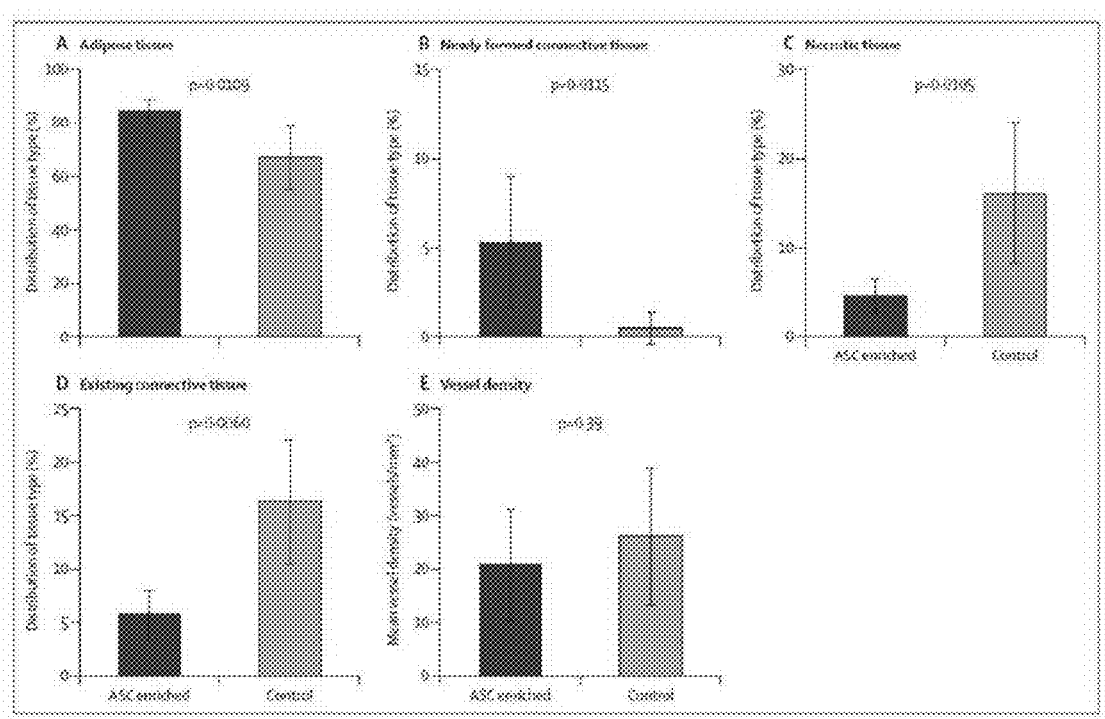

Castegnaro, et al., "Effect of Platelet Lysate on the Functional and Molecular Characteristics of Mesenchymal Stem Cells Isolated from Adipose Tissue", 2011, pp. 105-114, vol. 6., Current Stem Cell Research.

Naaijkens, et al., "Human platelet lysate as a fetal bovine serum substitute improves human adipose-derived stromal cell culture for future cardiac repair applications", 2012, pp. 119-130, vol. 348, Cell Tissue Res.

Laitinen, et al., "A robust and reproducible animal serum-free culture method for clinical-grade bone marrow-derived mesenchymal stromal cells", Mar. 17, 2015, pp. 1-16, Cytotechnology.

Hemeda, et al., "Evaluation of human platelet lysate versus fetal bovine serum for culture of mesenchymal stromal cells", 2014, pp. 170-180, vol. 16, Cytoherapy.

Amirkhani, et al., "Rejuvenation of facial skin and improvement in the dermal architecture by transplantation of autologous stromal vascular fraction: a clinical study", 2016, pp. 149-154, vol. 6, No. 3, Bioimpacts.

Astori, et al., ""In vitro" and multicolor phenotypic characterization of cell subpopulations identified in fresh human adipose tissue stromal vascular fraction and in the derived mesenchymal stem cells", 2007, pp. 1-10, vol. 5, No. 55, Journal of Translational Medicine.

Bieback, et al., "Altered Gene Expression in Human Adipose Stem Cells Cultured with Fetal Bovine Serum Compared to Human Supplements", 2010, pp. 3467-3484, vol. 16, No. 11, Tissue Engineering, Part A.

Dominici, et al., "Minimal criteria for defining multipotent mesenchymal stromal cells." The International Society for Cellular Therapy position statement, 2006, pp. 315-317, vol. 8, No. 4, Cytopherapy.

Maumus, et al., "Native human adipose stromal cells: localization morphology and phenotype", 2011, pp. 1141-1153, vol. 35, International Journal of Obesity.

Baer, "Adipose-derived mesenchymal stromal/stem cells: An update on their phenotype in vivo and in vitro." World Journal of Stem Cells, vol. 6(3), pp. 256-265 (2014).

Maumus, M. et al. (20110 "Native human adipose stromal cells: localization, morphology and phenotype," International Journal of Obesity 35:1141-1153.

Blande et al., "Adipose tissue mesenchymal stem cell expansion in animal serum-free medium supplemented with autologous human platelet lysate", Transplantation and Cellular Engineering, Transfusion, Dec. 2009, vol. 49, pp. 2680-2685.

Cholewa et al., "Expansion of Adipose Mesenchymal Stromal Cells Is Affected by Human Platelet Lysate and Plating Density", Cell Transplantation, 2011, vol. 20, pp. 1409-1422.

Crespo-Diaz et al., "Platelet Lysate Consisting of a Natural Repair Proteome Supports Human Mesenchymal Stem Cell Proliferation and Chromosomal Stability", Cell Transplantation, 2011, vol. 20, pp. 797-811.

Gottipamula et al., "Human platelet lysate is an alternative to fetal bovine serum for large-scale expansion of bone marrow-derived mesenchymal stromal cells", Biotechnol Lett, 2012, vol. 34, pp. 1367-1374.

Kocaoemer et al., "Human AB Serum and Thrombin-Activated Platelet-Rich Plasma Are Suitable Alternatives to Fetal Calf Serum for the Exapansion of Mesenchymal Stem Cells from Adipose Tissue", Stem Cells, 2007, 25, pp. 1270-1278.

Kolle et al., "Importance of mesenchymal stem cells in autologous fat grafting: A systematic review of existing studies", Journal of Plastic Surgery and Hand Surgery, 2012, vol. 46, pp. 59-68.

Kolle et al., "Pooled human platelet lysate versus fetal bovine serum-investigating the proliferation rate, chromosome stability and angiogenic potential of human adipose tissue-derived stem cells intended for clinical use", Cytotherapy, 2013, 15, pp. 1086-1097.

Lange et al., "Accelerated and Safe Expansion of Human Mesenchymal Stromal Cells in Animal Serum-Free Medium for Transplantation and Regenerative Medicine", Journal of Cellular Physiology, 2007, vol. 213, pp. 18-26.

Lange et al., "Platelet lysate suppresses tne expression of lipocaiin-type prostaglandin D2 synthase that positively controls adipogenic differentiation of human mesenchymal stromal cells", Experimental Cell Research, 2012, vol. 318, pp. 2284-2296.

Mirabet et al., "Human platelet lysate enhances the proliferative activity of cultured human fibroblast-like cells from different tissues", Cell Tissue Banking, 2008, vol. 9, pp. 1-10.

Pu et al., "The Fate of Cryopreserved Adipose Aspirates After in Vivo Transplantation", Asthetic Surgery Journal (2006), vol. 6, pp. 653-661.

Schallmoser et al., "Rapid Large-Scale Expansion of Functional Mesenchymal Stem Cells from Unmanipulated Bone Marrow Without Animal Serum", Tissue Engineering: Part C, vol. 14, No. 3, 2008, pp. 185-196.

Shih et al., "Expansion of adipose tissue mesenchymal stromal progenitors in serum-free medium supplemented with virally inactivated allogeneic human platelet lysate", Transfusion Practice, vol. 51, Apr. 2011, pp. 770-778.

Zhu et al., "Supplementation of fat grafts with adipose-derived regenerative cells improves long term graft retention" Ann. Plat. Surg. (2010) 64:222-228.

* cited by examiner

LIPOFILLING WITH EX-VIVO EXPANDED ADIPOSE TISSUE-DERIVED STEM CELLS FOR COSMETIC BREAST FILLING OR FOR FACIAL FILLING AND/OR REJUVENATION

FIELD OF THE INVENTION

The present invention relates to soft tissue filling with ex-vivo expanded adipose tissue-derived stem cells or ex-vivo expanded adipose tissue-derived stem cell enriched fat grafts. These may be used for cosmetic breast filling/augmentation or for facial filling and/or rejuvenation.

DESCRIPTION OF THE INVENTION

A frequent challenge in plastic surgery is the correction of volume defects and augmentation of existing volume. When correcting volume defects or when augmenting existing tissue, it is often necessary to use filling material, a so-called filler or an implant. Autologous fat grafting (lipofilling) enables repair and augmentation of soft tissues (e.g. cosmetic breast augmentation) and is increasingly used both in aesthetic and reconstructive surgery. Autologous fat tissue has been considered to be an ideal filler for augmentation of soft tissue because it is biocompatible, versatile, natural-appearing, non-immunogenic, inexpensive, and readily obtainable with low donor site morbidity[1,2]. The transplanted fat graft, however, has an unpredictable and often low survival, which is why investigators have sought new ways of increasing its viability. One animal study investigating xenogeneic fat grafting enriched with adipose tissue-derived mesenchymal stem cells (ASC) has indicated that the technique is valid and reproducible, and results in increased residual volume of the transplant compared to non-enriched[3]. A recent human study has demonstrated and confirmed the advantage and striking effect of adding ASCs to the fat graft for increased residual volume and better quality of the transplanted tissue[4].

In the cosmetic industry, the solutions available for cosmetic facial filling/rejuvenation are predominantly artificial (e.g. Botulinum Toxin Type A, Hyaluronic, Collagen, Calcium Hydroxylapatite, Polyactic acid, Polymethyl-methacrylate microspheres). Therefore, results often end up looking un-natural due to low versatility and bio-compatibility. The artificial fillers de-compose over time with possible adverse physical side-effects ranging from various sickness symptoms to beauty flaws. Autologous fat tissue is considered to be an ideal filler solution as described above. However, the outcomes for the patients treated with autologous fat for facial filling/rejuvenation (i.e. Without stem cell enrichment) may end up with disproportionate results, due to the unpredictable survival of the graft.

Some surgeons propose a better and more predictable graft take can be accomplished by adding the so-called stroll vascular fraction (SR4) to the transplant[5,6]. The SR4 is the cell pellet that forms when adipose tissue is harvested by liposuction and the fat cells are enzymatically digested using collagenase. The SR4 is known to contain a small amount of adipose tissue-derived stem cells (ASCs).

It is important to distinguish between the following terms:
1) Conventional lipofilling: Fat only
2) Cell-assisted lipotransfer: Fat+SR4
3) Stem cell enriched lipofilling: Fat+ex-vivo expanded ASCs
4) Stem cell filling: ex-vivo expanded ASCs In the current patent application, we only refer to terms 3) and 4) above.

Definition of the stem cells referred to in the current patent application: Cells adherent to a culture surface when seeding and culturing the stroll vascular fraction.

For both breast and facial applications autologous or allogeneic cells may be used.

The present invention is especially suitable for cosmetic facial filling and rejuvenation and for cosmetic breast filling/augmentation.

DETAILED DESCRIPTION OF THE INVENTION

The present invention relates to a composition comprising ex-vivo expanded adipose tissue-derived stem cell (ASC) or ex-vivo expanded adipose tissue-derived stem cells (ASC) mixed with harvested fat tissue at a ratio of $5.0 \times 10^4$-$2.0 \times 10^8$ ASCs/mL fat; for example $1.0 \times 10^5$-$2.0 \times 10^7$ and the use of ex-vivo expanded adipose tissue-derived stem cells or ex-vivo expanded adipose tissue-derived stem cell enriched fat grafts as an agent for cosmetic breast filling/augmentation or for facial filling/rejuvenation.

Surgical Procedure for Harvesting ASCs

Patients receive an outpatient minor liposuction.

Lipoaspirates will be harvested by standard sterile liposuction techniques. Through incisions a wetting solution is infiltrated into the subcutaneous fat. The lipoaspirate is procured with a standard liposuction device (e.g., VIBRASAT®) and sealed in a sterile container. The lipoaspirate is transported to the clinical stem cell laboratory.

Isolation and Culture of ASCs

ASC isolation and ex vivo expansion will be performed in accordance with an approved protocol, in a laboratory approved for good manufacturing practice (GMP) and clinical stem cell expansion, at a Cell Therapy Facility.

The lipoaspirate is washed with phosphate-buffered saline (PBS) and centrifuged. To isolate the Stroll vascular fraction (SR4), the supernatant is incubated and enzymatically digested with collagenase (GMP grade). The enzymatic activity is neutralized using growth medium. The suspension is filtered using a 60-100 μm filter and centrifuged. The cell pellet is resuspended in culturing medium and the cells in the pellet that contain the SR4 are counted. An alternative way of isolation the SR4 is using a closed system e.g. the GID SR4-1™ system. The SR4 is seeded in culture medium consisting of Dulbecco's modified Eagle's medium (DMEM) or Alpha minimal essential medium (α-MEM),1-5% penicillin-streptomycin, 1-5 IU/mL preservative-free heparin and 2-20% pooled Human Platelet Lysate pHPL or any other alternative growth medium e.g. Fetal Bovine Serum. The primary cultures (P0) are incubated. The non-adherent cells are discarded, the cell culture flasks are carefully rinsed with PBS, and the medium replaced. The medium is changed every 3-7 days. During culturing and on the day of ASC harvesting every culture flask/stack will be examined for pathogen contamination.

pHPL Production

The pHPL may be manufactured as described by Schallmoser et al.[7], with minor modifications. Briefly, after informed consent, whole blood units are collected from healthy blood donors. All of the blood donations are tested for infectious disease markers, in adherence with existing law. The buffy coats are separated from the red blood cells and plasma. Four buffy-coat units are pooled with 1 unit of plasma into 1 unit of platelet-rich plasma (PRP) and are stored at−20° C. to−80° C. Minimum ten units of PRP is thawed in a water bath and then pooled into a single PRP batch. The pooled PRP batch is aliquoted into smaller fractions and frozen at −20° C. to −80° C. Next, all of the aliquoted bags from the single, pooled PRP batch are thawed in a water bath and centrifuged (e.g. at 4000 g for 15 min) to sediment the platelet fragments. Lastly, the pHPL-containing supernatant is transferred into new bags and stored at −40° C. to −80° C. for later use in the preparation of the cell culture medium.

ASC Harvesting Procedure

ASCs are harvested in P0-P4. All cell culture flasks/stacks are washed with PBS and the cells are detached from the plastic surface using either chemical (e.g. Tryple Select) or physical processing. The suspension containing the ASCs is centrifuged (e.g. at 300 g for 5 min), the supernatant is removed and the cell pellet is collected after resuspension in PBS. The ASC cell pellet is washed with PBS, centrifuging the ASCs and discarding the supernatant after each washing procedure. Cells are counted three times and the average count will be calculated. ASCs will be carefully controlled before releasing them for clinical use, including 1) Absence of pathogen contamination 2) Viability of the ASCs greater than 90% 3) Morphology, assessed to be characteristic for ASCs. The ASCs will be transported in approved sterile containers.

Liposuction, Graft Preparation and Lipofilling Procedure

The surgical procedure is conducted under either local or general anesthesia. Lipoaspirates are harvested by standard sterile liposuction techniques. Through incisions a wetting solution (e.g. Kleins solution) is infiltrated into the donor site using a blunt infiltrator. The harvesting cannula is 2-5 mm in diameter with a blunt tip, connected to a harvesting device (e.g., VIBRASAT®). If needed the lipoaspirate is washed using saline. The harvested lipoaspirate is either left to sedimentate, spun or centrifuged (e.g. at 100 g for 5 min) After the separation procedure, the oil layer (upper level) is decanted and the aqueous layer (lower level) is also drained out of the syringes. The middle layer, composed of predominantly fat graft is used for transplantation.

The Invented Applications:

Cosmetic breast filling: The harvested fat tissue is mixed with the harvested ex-vivo expanded ASCs at a ratio of $5.0 \times 10^4$-$2.0 \times 10^8$ ASCs/mL fat, preferably at a ratio of $1.0 \times 10^5$-$2.0 \times 10^7$ ASCs/mL fat, and injected as aliquots into the breast for cosmetic augmentation.

Example of Injection Technique:

The enriched fat graft is injected to the breast using a long needle horizontally (parallel to the body) to avoid damaging structures outside the breast tissue. The needle is inserted from several points around the areola margin and at several points at the inframammary fold in variable directions and planes to achieve an even and natural appearing distribution of the graft.

For facial filling and wrinkle correction: The harvested fat tissue is mixed with the harvested ex-vivo expanded ASCs at a ratio of $5.0 \times 10^4$-$2.0 \times 10^8$ ASCs/mL fat for a standard filling, preferably at a ratio of $1.0 \times 10^5$-$2.0 \times 10^7$ ASCs/mL fat. The amount of stem cells will be increased depending on the amount of filling needed, the less filling is needed, the higher the concentration of ASCs. If the desired effect is purely a matter of tissue quality improvement, ASCs alone will be used, solved in PBS in order to evenly distribute the cells.

Example of Injection Technique:

When used as a filler the fat grafts are injected as aliquots with a long needle horizontally (parallel to the surface) to avoid damaging structures outside the target area. The needle is inserted from several points and in variable directions and planes to achieve an even and natural appearing distribution of the graft.

When used purely for tissue quality improvement, the solved ASCs are injected in the dermis and subdermal with a thin sharp needle and evenly distributed in the target area. The incision and injection sites are sutured and postoperative compression garments are applied to the donor sites and in some cases also to the recipient sites.

Clinical Benefits and Novelty of the Invention

ASC (ex-vivo expanded) enriched fat grafts or ASCs alone have never been used clinically for injection in the breast or in the face and has never been described in the literature nor has the inventor shared the idea of these clinical applications with others prior to the patent submission of U.S. 61/839,578. The idea of enriching fat grafts with ex-vivo expanded ASCs in order to improve survival and quality of the fat grafts has been demonstrated in a murine model[3] and in a recent proof of concept study in humans[4], though as mentioned above the clinical applications of this invention has never been demonstrated (i.e. cosmetic breast filling and facial filling). It should be stressed that this invention (i.e. the application of ex-vivo expanded ASCs for the purpose of facial filling/rejuvenation and cosmetic breast filling/augmentation) is significantly different from the use of freshly isolated SR4, including a small fraction of non-expanded ASCs, for conventional so called "cell assisted lipo-filling". This method has been described in the literature and applied in humans with unpredictable clinical outcomes, not significantly better than conventional lipofilling[8]. The rationale for using ex-vivo expanded ASCs for facial filling is supported by the studies mentioned above, where it is demonstrated that stem cells survive after injection as opposed to fat cells. Additionally ASCs are very resistant to hypoxia and physical exposures[9-11]. By using stem cells alone as filling material a reliable residual volume/augmentation can be achieved.

There are many clinical benefits from making a biocompatible sustainable breast and facial filler, including natural appearance, non-immunogenicity, avoiding the side effects of artificial material and the procedure can be autologous. Most patients have natural fat reserves on the abdomen, thighs, arms and buttocks, which can be used. In this way the patients get a customized and desired body re-sculpturing. Autologous adipose tissue can easily be transplanted by simple liposuction and subsequent injection, with very little discomfort for the patients and with very little risks of side effects.

EXAMPLES

Research Results—Proof of Concept Study (analogous to the study design described in e.g. Kolle S F, Fischer-Nielsen A, Mathiasen A B, et al. Enrichment of autologous fat grafts with ex-vivo expanded adipose tissue-derived stem cells for graft survival: a randomised placebo-controlled trial. Lancet 2013; 382: 1113-20):

Aim of the Study:

Fat grafts enriched with high dose autologous ex-vivo expanded adipose tissue-derived stem cells (ASCs) is compared to Non-enriched fat grafts (conventional fat grafting).

Study Design:

Purified fat grafts, one with and one without ASC enrichment (control) are prepared for each participant. The fat grafts are injected subcutaneously.

A concentration of $20 \times 10^6$ ASCs per mL enriched fat graft is chosen—approximately 2,000 times the physiological level.

The volumes of the injected fat grafts are measured by magnetic resonance imaging (MRI) immediately after injection and after 121 days and compared to the baseline MRI.

Result:

Compared with the control grafts, the ASC-enriched fat grafts have significantly higher residual volumes. No serious adverse events have been observed.

Aspects:

In accordance with the above the present invention can be further described by the following aspects, in which a reference to stem cells is to be understood as a reference to both autologous and allogeneic cells unless specified to the contrary.

1. Ex-vivo expanded adipose tissue-derived stem cell enriched fat grafts for use in a method of breast filling.

2. Ex-vivo expanded adipose tissue-derived stem cell enriched fat grafts or ex-vivo expanded adipose tissue-derived stem cells for use in a method of facial filling.

3. A composition comprising ex-vivo expanded adipose tissue-derived stem cell (ASC) enriched fat grafts or ex-vivo expanded adipose tissue-derived stem cells (ASC) mixed with harvested fat tissue at a ratio of $5.0 \times 10^4$-$2.0 \times 10^8$ ASCs/mL fat.

4. Use of ex-vivo expanded adipose tissue-derived stem cell enriched fat grafts for breast filling.

5. Use of ex-vivo expanded adipose tissue-derived stem cell enriched fat grafts or ex-vivo expanded adipose tissue-derived stem cells for facial filling.

6. Use of ex-vivo expanded adipose tissue-derived stem cell enriched fat grafts as a breast filling agent.

7. Use of ex-vivo expanded adipose tissue-derived stem cell enriched fat grafts or ex-vivo expanded adipose tissue-derived stem cells as a facial filling agent.

8. Use of ex-vivo expanded adipose tissue-derived stem cell enriched fat grafts or ex-vivo expanded adipose tissue-derived stem cells for cosmetic breast filling.

9. Use of ex-vivo expanded adipose tissue-derived stem cell enriched fat grafts or ex-vivo expanded adipose tissue-derived stem cells for cosmetic facial filling.

10. Use of ex-vivo expanded adipose tissue-derived stem cell enriched fat grafts or ex-vivo expanded adipose tissue-derived stem cells in the manufacture of a medicament for the treatment of signs of aging.

11. Method of breast filling wherein adipose tissue-derived stem cell (ASC) enriched fat grafts is mixed with harvested fat tissue at a ratio of $5.0 \times 10^4$-$2.0 \times 10^8$ ASCs/mL fat, and wherein the fat is injected as aliquots or as strings with a long needle horizontally (parallel to the body) by inserting the needle from several points around the areola margin and at several points at the inframammary fold in variable directions and planes to achieve an even and natural appearing distribution of the graft.

12. Method of facial filling wherein expanded adipose tissue-derived stem cell (ASC) enriched fat grafts or ex-vivo expanded adipose tissue-derived stem cells (ASC) are mixed with harvested fat tissue at a ratio of $5.0 \times 10^4$-$2.0 \times 10^8$ ASCs/mL fat or solved in PBS in order to evenly distribute the cells, and wherein the fat grafts are injected as aliquots or as strings with a long needle horizontally (parallel to the surface) to avoid damaging structures outside the target area and the needle is inserted from several points and in variable directions and planes to achieve an even and natural appearing distribution of the graft.

13. Method of facial filling wherein expanded adipose tissue-derived stem cell (ASC) enriched fat grafts or ex-vivo expanded adipose tissue-derived stem cells (ASC) are mixed with harvested fat tissue at a ratio of $5.0 \times 10^4$-$2.0 \times 10^8$ ASCs/mL fat or solved in PBS in order to evenly distribute the cells, and wherein the solved ASCs are injected in the dermis with a thin sharp needle and evenly distributed in the target area and the incision and injection sites are sutured and postoperative compression garments are applied to the donor sites and in some cases also to the recipient sites.

14. Cosmetic method of breast filling wherein adipose tissue-derived stem cell (ASC) enriched fat grafts is mixed with harvested fat tissue at a ratio of $5.0 \times 10^4$-$2.0 \times 10^8$ ASCs/mL fat, and wherein the fat is injected as aliquots or as strings with a long needle horizontally (parallel to the body) by inserting the needle from several points around the areola margin and at several points at the inframammary fold in variable directions and planes to achieve an even and natural appearing distribution of the graft.

15. Cosmetic method of facial filling wherein expanded adipose tissue-derived stem cell (ASC) enriched fat grafts or ex-vivo expanded adipose tissue-derived stem cells (ASC) are mixed with harvested fat tissue at a ratio of $5.0 \times 10^4$-$2.0 \times 10^8$ ASCs/mL fat or solved in PBS in order to evenly distribute the cells, and wherein the fat grafts are injected as aliquots or as strings with a long needle horizontally (parallel to the surface) to avoid damaging structures outside the target area and the needle is inserted from several points and in variable directions and planes to achieve an even and natural appearing distribution of the graft.

16. Cosmetic method of facial filling wherein expanded adipose tissue-derived stem cell (ASC) enriched fat grafts or ex-vivo expanded adipose tissue-derived stem cells (ASC) are mixed with harvested fat tissue at a ratio of $5.0 \times 10^4$-$2.0 \times 10^8$ ASCs/mL fat or solved in PBS in order to evenly distribute the cells, and wherein the solved ASCs are injected in the dermis with a thin sharp needle and evenly distributed in the target area and the incision and injection sites are sutured and postoperative compression garments are applied to the donor sites and in some cases also to the recipient sites.

17. Cosmetic method of introducing an agent to the skin wherein the agent comprises ex-vivo expanded adipose tissue-derived stem cell enriched fat grafts or ex-vivo expanded adipose tissue-derived stem cells.

18. Cosmetic method of introducing an agent to the skin wherein the agent comprises ex-vivo expanded adipose tissue-derived stem cell (ASC) enriched fat grafts or ex-vivo expanded adipose tissue-derived stem cells (ASC) mixed with harvested fat tissue at a ratio of $5.0 \times 10^4$-$2.0 \times 10^8$ ASCs/mL fat.

19. A method of lipofilling the skin by the use of ex-vivo expanded adipose tissue-derived stem cell enriched fat grafts or ex-vivo expanded adipose tissue-derived stem cells.

20. A method of lipofilling the skin by the use of a composition comprising ex-vivo expanded adipose tissue-derived stem cell (ASC) enriched fat grafts or ex-vivo expanded adipose tissue-derived stem cells (ASC) mixed with harvested fat tissue at a ratio of $5.0 \times 10^4$-$2.0 \times 10^8$ ASCs/mL fat.

REFERENCES

1 Leuchter I, Schweizer V, Hohlfeld J, Pasche P. Treatment of velopharyngeal insufficiency by autologous fat injection. Eur Arch Otorhinolaryngol 2010; 267: 977-83.

2 Coleman SR. Structural fat grafts: the ideal filler? Clin Plast Surg 2001; 28:111-9.

3 Lu F, Li J, Gao J, et al. Improvement of the survival of human autologous fat transplantation by using VEGF-transfected adipose-derived stem cells. Plast Reconstr Surg 2009; 124: 1437-46.

4 Kolle S F, Fischer-Nielsen A, Mathiasen A B, et al. Enrichment of autologous fat grafts with ex-vivo expanded adipose tissue-derived stem cells for graft survival: a randomised placebo-controlled trial. Lancet 2013; 382: 1113-20.

5 Yoshimura K, Sato K, Aoi N, Kurita M, Hirohi T, Harii K. Cell-assisted lipotransfer for cosmetic breast augmentation: supportive use of adipose-derived stem/stroll cells. Aesthetic Plast Surg 2008; 32: 48-55.

6 Matsumoto D, Sato K, Gonda K, et al. Cell-assisted lipotransfer: supportive use of human adipose-derived cells for soft tissue augmentation with lipoinjection. Tissue Eng 2006; 12: 3375-82.

7 Schallmoser K, Bartmann C, Rohde E, et al. Human platelet lysate can replace fetal bovine serum for clinical-scale expansion of functional mesenchymal stroll cells. Transfusion 2007; 47: 1436-46.

8 Peltoniemi H H, Salmi A, Miettinen S, et al. Stem cell enrichment does not warrant a higher graft survival in lipofilling of the breast: a prospective comparative study. J Plast Reconstr Aesthet Surg 2013; 66: 1494-503.

9 Rehman J, Traktuev D, Li J, et al. Secretion of angiogenic and antiapoptotic factors by human adipose stroll cells. Circulation 2004; 109: 1292-8.

10 Rasmussen J G, Frobert O, Pilgaard L, et al. Prolonged hypoxic culture and trypsinization increase the pro-angiogenic potential of human adipose tissue-derived stem cells. Cytotherapy 2010.

11 Thangarajah H, Vial I N, Chang E, et al. IFATS collection: adipose stroll cells adopt a proangiogenic phenotype under the influence of hypoxia. Stem Cells 2009; 27: 266-74.

The invention claimed is:

1. A composition of at least 1 mL in volume comprising ex-vivo expanded adipose tissue-derived stem cells (ASCs) mixed with harvested fat tissue at a ratio of at least $20 \times 10^6$ ASCs/mL fat, wherein said ex-vivo expanded adipose tissue-derived stem cells (ASCs) have been cultured in a growth medium consisting of Dulbecco's modified Eagle's medium (DMEM) or Alpha minimal essential medium (a-MEM), 1-5% penicillin-streptomycin, 1-5 IU/mL preservative-free heparin and 10-20% pooled Human Platelet Lysate (pHPL) for at least 3 to 7 days, wherein said ex-vivo expanded adipose tissue-derived stem cells (ASCs) display a homogenous morphology, are adherent to a plastic culture surface, and are negative for the hematopoietic surface marker CD34.

2. A composition according to claim 1 formulated for use as a breast filling agent, a facial filling agent, for cosmetic breast filling, or for cosmetic facial filling.

3. The composition of claim 1, wherein the adipose tissue-derived stem cells (ASCs) are human ASCs and the harvested fat tissue is human fat tissue.

4. The method composition of claim 1 or 3, wherein the expanded ASCs are harvested in the primary passage (P0).

5. A method for tissue reconstruction comprising administration of the composition according to claim 1 or 3 to a subject.

6. The method of claim 5, wherein the tissue reconstruction is selected from breast filling, facial filling, cosmetic breast filling, or cosmetic facial filing.

7. The method of claim 5, wherein the subject is a human patient.

* * * * *